(12) United States Patent
Ma et al.

(10) Patent No.: US 8,635,042 B2
(45) Date of Patent: Jan. 21, 2014

(54) SEMI-AUTOMATIC DEVICE CALIBRATION

(75) Inventors: Dung Ma, Westminster, CA (US); Abraham Hajishah, Irvine, CA (US); James Gerg, Lake Forest, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 877 days.

(21) Appl. No.: 12/613,595

(22) Filed: Nov. 6, 2009

(65) Prior Publication Data
US 2011/0092962 A1    Apr. 21, 2011

Related U.S. Application Data

(60) Provisional application No. 61/112,536, filed on Nov. 7, 2008.

(51) Int. Cl.
*G01C 17/38* (2006.01)
(52) U.S. Cl.
USPC .............................. 702/94; 702/151
(58) Field of Classification Search
USPC .................... 702/85, 87, 88, 94, 150, 151
See application file for complete search history.

(56) References Cited

U.S. PATENT DOCUMENTS

| | | | |
|---|---|---|---|
| 1,848,024 A | 3/1932 | Owen | |
| 3,076,904 A | 2/1963 | Claus et al. | |
| 3,116,697 A | 1/1964 | Theodore | |
| 3,526,219 A | 9/1970 | Balamuth | |
| 3,781,142 A | 12/1973 | Zweig | |
| 3,857,387 A | 12/1974 | Shock | |
| 4,037,491 A | 7/1977 | Newbold | |
| 4,189,286 A | 2/1980 | Murry et al. | |
| 4,193,004 A | 3/1980 | Lobdell et al. | |
| 4,564,342 A | 1/1986 | Weber et al. | |
| 4,757,814 A | 7/1988 | Wang et al. | |
| 4,773,897 A | 9/1988 | Scheller et al. | |
| 4,837,857 A | 6/1989 | Scheller et al. | |
| 4,920,336 A | 4/1990 | Meijer | |
| 4,954,960 A | 9/1990 | Lo et al. | |
| 4,965,417 A | 10/1990 | Massie | |
| 4,983,901 A | 1/1991 | Lehmer | |

(Continued)

FOREIGN PATENT DOCUMENTS

| | | |
|---|---|---|
| EP | 56019 A1 | 7/1982 |
| EP | 619993 A1 | 10/1994 |

(Continued)

OTHER PUBLICATIONS

International Search Report for Application No. PCT/US07/083875, mailed on May 7, 2008, 4 pages.

(Continued)

*Primary Examiner* — Manuel L Barbee
(74) *Attorney, Agent, or Firm* — Abbott Medical Optics Inc.

(57) ABSTRACT

A method and apparatus for calibrating a medical device operable in at least one axis of movement, such as a footpedal or footswitch, is provided. The design includes instructing a user to operate the device to a first predetermined position in a first axis of movement while concurrently monitoring movement of the device to establish a set of movement responses, prompting the user to indicate when the first predetermined position in the first axis is attained modifying the set of movement responses when movement response irregularities are detected, thereby establishing a modified set of movement responses, and employing the modified set of movement responses during a medical procedure.

25 Claims, 7 Drawing Sheets

(56) References Cited

U.S. PATENT DOCUMENTS

| | | | |
|---|---|---|---|
| 5,006,110 A | 4/1991 | Garrison et al. |
| 5,026,387 A | 6/1991 | Thomas |
| 5,039,973 A | 8/1991 | Carballo |
| 5,091,656 A | 2/1992 | Gahn |
| 5,125,891 A | 6/1992 | Hossain et al. |
| 5,160,317 A | 11/1992 | Costin |
| 5,195,960 A | 3/1993 | Hossain et al. |
| 5,195,961 A | 3/1993 | Takahashi et al. |
| 5,195,971 A | 3/1993 | Sirhan |
| 5,230,614 A | 7/1993 | Zanger et al. |
| 5,268,624 A * | 12/1993 | Zanger .................. 318/551 |
| 5,282,787 A | 2/1994 | Wortrich |
| 5,323,543 A | 6/1994 | Steen et al. |
| 5,342,293 A | 8/1994 | Zanger |
| 5,454,783 A | 10/1995 | Grieshaber et al. |
| 5,470,211 A | 11/1995 | Knott et al. |
| 5,520,652 A | 5/1996 | Peterson |
| 5,549,461 A | 8/1996 | Newland |
| 5,554,894 A | 9/1996 | Sepielli |
| 5,580,347 A | 12/1996 | Reimels |
| 5,591,127 A | 1/1997 | Barwick, Jr. et al. |
| 5,657,000 A | 8/1997 | Ellingboe |
| 5,676,530 A | 10/1997 | Nazarifar |
| 5,676,650 A | 10/1997 | Grieshaber et al. |
| 5,693,020 A | 12/1997 | Rauh |
| 5,697,898 A | 12/1997 | Devine |
| 5,700,240 A | 12/1997 | Barwick, Jr. et al. |
| 5,733,256 A | 3/1998 | Costin |
| 5,745,647 A | 4/1998 | Krause |
| 5,747,824 A | 5/1998 | Jung et al. |
| 5,830,176 A | 11/1998 | Mackool |
| 5,843,109 A | 12/1998 | Mehta et al. |
| 5,899,674 A | 5/1999 | Jung et al. |
| 5,928,257 A | 7/1999 | Kablik et al. |
| 5,983,749 A | 11/1999 | Holtorf |
| 6,002,484 A | 12/1999 | Rozema et al. |
| 6,024,428 A | 2/2000 | Uchikata |
| 6,062,829 A | 5/2000 | Ognier |
| 6,077,285 A | 6/2000 | Boukhny |
| 6,086,598 A | 7/2000 | Appelbaum et al. |
| 6,117,126 A | 9/2000 | Appelbaum et al. |
| 6,150,623 A | 11/2000 | Chen |
| 6,179,829 B1 | 1/2001 | Bisch et al. |
| 6,251,113 B1 | 6/2001 | Appelbaum et al. |
| 6,260,434 B1 | 7/2001 | Holtorf |
| 6,360,630 B2 | 3/2002 | Holtorf |
| 6,436,072 B1 | 8/2002 | Kullas et al. |
| 6,452,120 B1 | 9/2002 | Chen |
| 6,452,123 B1 | 9/2002 | Chen |
| 6,491,661 B1 | 12/2002 | Boukhny et al. |
| 6,511,454 B1 | 1/2003 | Nakao et al. |
| 6,632,214 B2 | 10/2003 | Morgan et al. |
| 6,674,030 B2 | 1/2004 | Chen et al. |
| 6,852,092 B2 | 2/2005 | Kadziauskas et al. |
| 6,862,951 B2 | 3/2005 | Peterson et al. |
| 6,962,488 B2 | 11/2005 | Davis et al. |
| 7,012,203 B2 | 3/2006 | Hanson et al. |
| 7,070,578 B2 | 7/2006 | Leukanech et al. |
| 7,169,123 B2 | 1/2007 | Kadziauskas et al. |
| 7,244,240 B2 | 7/2007 | Nazarifar et al. |
| 7,300,264 B2 | 11/2007 | Souza |
| 7,316,664 B2 | 1/2008 | Kadziauskas et al. |
| 7,381,917 B2 * | 6/2008 | Dacquay et al. ............. 200/86.5 |
| 7,439,463 B2 | 10/2008 | Brenner et al. |
| 7,470,277 B2 | 12/2008 | Finlay et al. |
| 2001/0023331 A1 | 9/2001 | Kanda et al. |
| 2001/0047166 A1 | 11/2001 | Wuchinich |
| 2001/0051788 A1 | 12/2001 | Paukovits et al. |
| 2002/0019607 A1 | 2/2002 | Bui |
| 2002/0070840 A1 | 6/2002 | Fischer et al. |
| 2002/0137007 A1 | 9/2002 | Beerstecher |
| 2002/0179462 A1 | 12/2002 | Silvers |
| 2003/0073980 A1 | 4/2003 | Finlay et al. |
| 2003/0108429 A1 | 6/2003 | Angelini et al. |
| 2003/0125717 A1 | 7/2003 | Whitman |
| 2004/0037724 A1 | 2/2004 | Haser et al. |
| 2004/0068300 A1 | 4/2004 | Kadziauskas et al. |
| 2004/0092922 A1 | 5/2004 | Kadziauskas et al. |
| 2005/0054971 A1 | 3/2005 | Steen et al. |
| 2005/0069419 A1 | 3/2005 | Cull et al. |
| 2005/0070859 A1 | 3/2005 | Cull et al. |
| 2005/0109595 A1 | 5/2005 | Mezhinsky et al. |
| 2005/0118048 A1 | 6/2005 | Traxinger |
| 2005/0209560 A1 | 9/2005 | Boukhny et al. |
| 2005/0245888 A1 | 11/2005 | Cull |
| 2005/0261628 A1 | 11/2005 | Boukhny et al. |
| 2006/0036180 A1 | 2/2006 | Boukhny et al. |
| 2006/0078448 A1 | 4/2006 | Holden |
| 2006/0145540 A1 | 7/2006 | Mezhinsky |
| 2006/0219049 A1 | 10/2006 | Horvath et al. |
| 2006/0236242 A1 | 10/2006 | Boukhny et al. |
| 2007/0016174 A1 | 1/2007 | Millman et al. |
| 2007/0049898 A1 | 3/2007 | Hopkins et al. |
| 2007/0060926 A1 | 3/2007 | Escaf |
| 2007/0073214 A1 | 3/2007 | Dacquay et al. |
| 2007/0078379 A1 | 4/2007 | Boukhny et al. |
| 2007/0249942 A1 | 10/2007 | Salehi et al. |
| 2008/0033342 A1 | 2/2008 | Staggs |
| 2008/0066542 A1 | 3/2008 | Gao |
| 2008/0067046 A1 | 3/2008 | Dacquay et al. |
| 2008/0112828 A1 | 5/2008 | Muri et al. |
| 2008/0114289 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1 | 5/2008 | Muri et al. |
| 2008/0114312 A1 | 5/2008 | Muri et al. |
| 2008/0114372 A1 | 5/2008 | Edwards et al. |
| 2008/0114387 A1 | 5/2008 | Hertweck et al. |
| 2008/0125697 A1 | 5/2008 | Gao |
| 2008/0125698 A1 | 5/2008 | Gerg et al. |
| 2008/0146989 A1 | 6/2008 | Zacharias |
| 2008/0262476 A1 | 10/2008 | Krause et al. |
| 2008/0281253 A1 | 11/2008 | Injev et al. |
| 2008/0294087 A1 | 11/2008 | Steen et al. |
| 2009/0005712 A1 | 1/2009 | Raney |
| 2009/0005789 A1 | 1/2009 | Charles |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0098721 A1 | 4/2011 | Tran et al. |
| 2011/0160646 A1 | 6/2011 | Kadziauskas et al. |

FOREIGN PATENT DOCUMENTS

| | | |
|---|---|---|
| EP | 1010437 A1 | 6/2000 |
| EP | 1310267 A2 | 5/2003 |
| EP | 1704839 A1 | 9/2006 |
| EP | 1787606 A1 | 5/2007 |
| EP | 1849443 A1 | 10/2007 |
| EP | 1849444 A1 | 10/2007 |
| EP | 1867349 A1 | 12/2007 |
| EP | 1873501 A1 | 1/2008 |
| EP | 1900347 A1 | 3/2008 |
| EP | 1925274 A2 | 5/2008 |
| ES | 2264369 A1 | 12/2006 |
| GB | 2230301 A | 10/1990 |
| JP | 2008188110 A | 8/2008 |
| WO | WO9220310 A1 | 11/1992 |
| WO | WO9317729 A1 | 9/1993 |
| WO | WO9324082 A1 | 12/1993 |
| WO | WO9632144 A1 | 10/1996 |
| WO | WO9818507 A1 | 5/1998 |
| WO | WO9917818 A1 | 4/1999 |
| WO | WO0000096 A1 | 1/2000 |
| WO | WO0070225 A1 | 11/2000 |
| WO | WO0234314 A1 | 5/2002 |
| WO | WO2005084728 A2 | 9/2005 |
| WO | WO2005092023 A2 | 10/2005 |
| WO | WO2005092047 A2 | 10/2005 |
| WO | WO2006101908 A2 | 9/2006 |
| WO | WO 2006/125280 A1 | 11/2006 |
| WO | WO2007121144 A1 | 10/2007 |
| WO | WO2007143677 A2 | 12/2007 |

(56) References Cited

FOREIGN PATENT DOCUMENTS

| WO | WO2007143797 A1 | 12/2007 |
|----|-----------------|---------|
| WO | WO2008030872 A1 | 3/2008  |
| WO | WO2008060859 A1 | 5/2008  |
| WO | WO2008060902 A1 | 5/2008  |
| WO | WO2008060995 A1 | 5/2008  |
| WO | WO2010054146 A1 | 5/2010  |
| WO | WO2010054225 A2 | 5/2010  |

OTHER PUBLICATIONS

International Search Report for Application No. PCT/US07/083880, mailed on May 30, 2008, 4 pages.
International Search Report for Application No. PCT/US07/084157, mailed on Apr. 1, 2008, 3 pages.
International Search Report for Application No. PCT/US07/084163, mailed on Apr. 1, 2008, 3 pages.
International Search Report for Application No. PCT/US08/064240, mailed on Oct. 19, 2008, 3 pages.
International Search Report for Application No. PCT/US08/071704, mailed on Nov. 26, 2008, 3 pages.
International Search Report for Application No. PCT/US08/072974, mailed on Feb. 23, 2009, 2 pages.
International Search Report for Application No. PCT/US2009/052473, mailed on Nov. 2, 2009, 3 pages.
"Phacoemulsification. Oct. 12, 2006. Wikipedia.com. Jun. 19, 2009 <http://en.wikipedia.org/wiki/Phacoemulsification>,".

\* cited by examiner

SEMI-AUTOMATIC DEVICE CALIBRATION

BACKGROUND OF THE INVENTION

1. Field of the Invention

The present invention relates generally to medical devices, and more specifically to calibrating devices employed in a medical or operating room setting, such as footswitches or footpedals.

2. Description of the Related Art

Today's safety critical systems, such as automated medical system products or surgical equipment, may be constructed as a collection of independent components realized in hardware and software. Constructing a suite of independent components or modules affords medical system product designers and manufacturers the ability to create and deploy subsystems that perform specific functions that are a subset of the complete device or system.

One such subsystem is that of a footswitch or footpedal, employed in certain medical environments, such as an operating room theater, in conjunction with a medical procedure such as a phacoemulsification ("phaco") surgical procedure. The footswitch is frequently employed to control phaco functionality, including but not limited to amount of power provided by the phaco needle, fluid flow aspects, and so forth.

Certain newer footswitches are dual-axis or dual linear footswitches, providing the user with two axes of control, commonly called the pitch axis and the yaw axis. A surgeon or operator can control one or more parameters in the pitch axis and one or more parameters in the yaw axis, so pushing down on the footswitch may provide a different function from moving one's foot to one side. Other inputs may be provided, such as buttons that can be depressed by the surgeon's foot, typically positioned away from the pedal or at the base of the pedal. A dual linear footswitch comprises a pitch axis and yaw axis and may provide a linear response, a panel response, a switch response, or any other response known in the art.

Overall system integrity is paramount to designing and deploying safety critical systems. Today's designers are faced with a difficult and complex implementation challenge to ensure a high level of performance in subsystems such as a footswitch in order to provide the required level of safety in an operating theater environment.

One issue that occurs with footswitches is falling out of alignment, or losing calibration. Electro-mechanical misalignment results from aging electronic components or dislocation of mechanical devices. Once a footswitch goes "out of alignment," which is generally a subjective determination, the footswitch is typically removed from service and repaired. Time away from the operating room environment is undesirable for any non-consumable medical device, such as a footswitch.

Based on the foregoing, it would be advantageous to provide a footswitch that has minimal or no downtime in most situations, or in other words a footswitch that overcomes the foregoing drawbacks present in previously known footswitches or similar medical devices.

SUMMARY OF THE INVENTION

According to one aspect of the present design, there is provided a method for calibrating a medical device operable in at least one axis of movement, such as a footpedal or footswitch. The method includes instructing a user to operate the device to a first predetermined position in a first axis of movement while concurrently monitoring movement of the device to establish a set of movement responses, prompting the user to indicate when the first predetermined position in the first axis is attained, modifying the set of movement responses when movement response irregularities are detected, thereby establishing a modified set of movement responses, and employing the modified set of movement responses during a medical procedure.

According to another aspect of the present design, there is provided a medical device operable in at least one axis of movement and a host device coupled with the medical device. The host device comprises a monitor configured to monitor movement of the medical device in the at least one axis of movement and establish a set of movement responses of the medical device and an application configured to receive the set of movement responses from the monitor and modify the set of movement responses when movement response irregularities are detected, thereby establishing a modified set of movement responses. The modified set of movement responses is configured to be employed with the medical device.

These and other advantages of the present invention will become apparent to those skilled in the art from the following detailed description of the invention and the accompanying drawings.

DESCRIPTION OF THE DRAWINGS

The present invention is illustrated by way of example, and not by way of limitation, in the figures of the accompanying drawings in which.

DETAILED DESCRIPTION OF THE INVENTION

The present design provides a method and apparatus for calibrating a medical device operable in at least one axis of movement, such as a footpedal or footswitch. The design includes instructing a user to operate the device to a first predetermined position in a first axis of movement while concurrently monitoring movement of the device to establish a set of movement responses, prompting the user to indicate when the first predetermined position in the first axis is attained, modifying the set of movement responses when movement response irregularities are detected, thereby establishing a modified set of movement responses, and applying the modified set of movement responses to the medical device.

While the present design may be used in various environments and applications, it will be discussed herein with a particular emphasis on a medical or hospital environment, where a surgeon or health care practitioner performs. For example, one embodiment of the present design is a phacoemulsification system or method that incorporates a device, such as a dual linear axis footswitch, to control the surgical system. As used herein, the terms "footpedal" and "footswitch" will be used relatively interchangeably and both mean a control device operable by a user's foot in normal operation.

Figure 1:
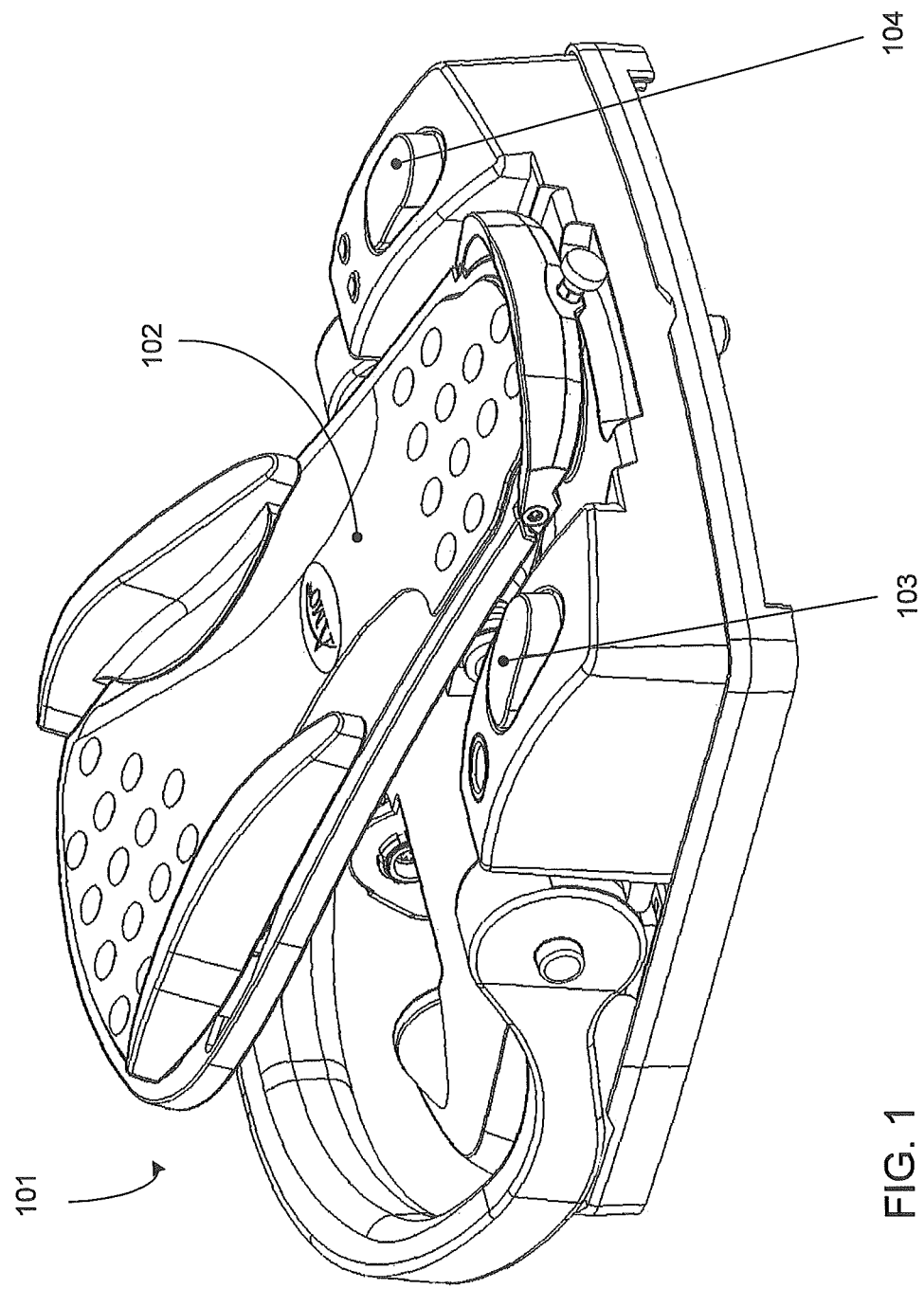
FIG. 1 illustrates a representative dual linear footpedal or footswitch.

FIG. 1 illustrates a typical dual linear axis footswitch 101. The pedal 102 can be depressed by a user to offer control of a parameter in the "pitch" direction, and the user twisting her foot can control a different parameter in the "yaw" direction. Switches 103 and 104 provide for additional control functionality.

One issue with existing footswitches such as that shown in FIG. 1 is that they can fall out of electro-mechanical alignment. Falling out of alignment may be judged by different metrics, and certain personnel may consider an alignment unacceptable that others would consider acceptable. Depending on circumstances, a footpedal may be considered out of alignment when complaints about the footswitch are received, or footswitches may be periodically evaluated based on a set of established criteria, and failure to meet certain criteria may result in the footswitch being considered out of alignment.

Alignment errors may take the form of dead zones or nonlinearities in certain regions of the two axes. When a footswitch such as footswitch 101 is considered out of alignment, the footswitch has in the past been taken off-line or out of the operating room environment and sent for repair, which typically entails taking footswitch 101 apart and swapping out faulty electrical and/or mechanical components, and such down time is generally undesirable.

Figure 2:
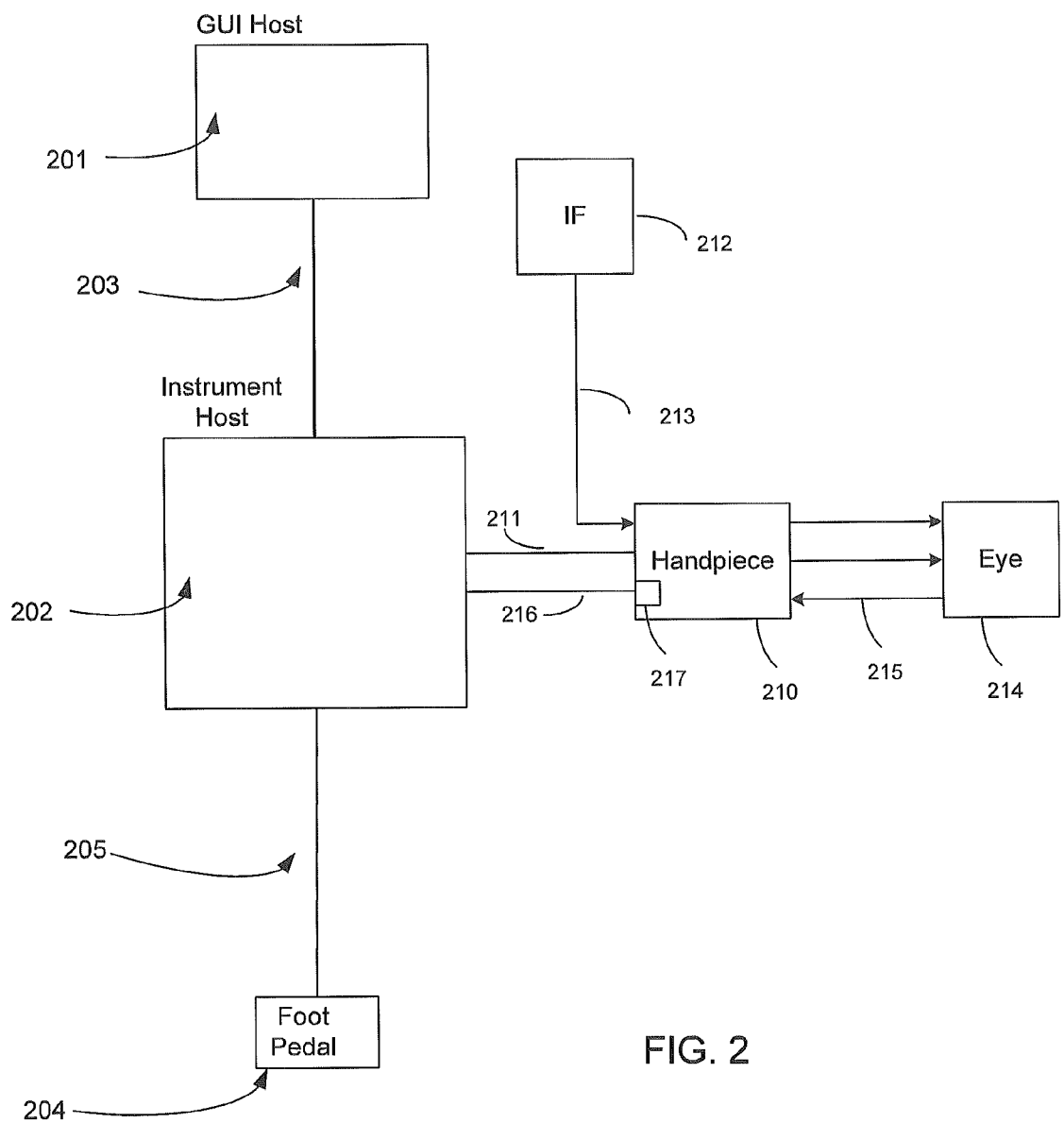
FIG. 2 is a block diagram illustrating various medical components in an ophthalmic surgical device, including a footpedal or footswitch.

FIG. 2 illustrates a phacoemulsification system in block diagram form showing components and interfaces for a medical system that may employ the present design. The particular embodiment illustrated in FIG. 2 contemplates that GUI host 201 and instrument host 202 are connected by a serial communication cable 203 for the purposes of controlling surgical instrument host 202. Note that while shown as two separate components in FIG. 2, GUI host 201 and instrument host 202 may be formed or provided in a single host device. A footswitch 204 is connected via a wire 205 or may be wirelessly connected (not shown) to surgical instrument host 202, wherein controls signals relating internal physical and virtual switch position information are transmitted to the instrument host 202.

A phacoemulsification system such as that shown in FIG. 2 has a handpiece/needle 210 that includes a needle and electrical means, typically a piezoelectric crystal, for ultrasonically vibrating the needle. Instrument host 202 supplies power on line 211 to handpiece/needle 210. An irrigation fluid source 212 is fluidly coupled to handpiece/needle 210 through line 213. The irrigation fluid and ultrasonic power are applied by handpiece/needle 210 to an eye or affected area or region, indicated diagrammatically as eye 214. Alternatively, the irrigation source may be routed to eye 214 through a separate pathway independent of the handpiece.

The eye 214 is aspirated by one or more pumps (not shown) in instrument host 202 through line/handpiece needle 215 and line 216. A switch 217 may be provided on the handpiece 210 and may provide a means for enabling a surgeon/operator to select an amplitude of electrical pulses to the handpiece via the instrument host and GUI host. Switch 217 may be omitted, and footswitch 204 or other device may be utilized in lieu of switch 217. Footswitch 204 may control fluid flow and/or ultrasonic parameters as desired, and as discussed herein, a dual axis linear footswitch may be employed as footswitch 204.

In FIG. 2, footswitch 204 and instrument host 202 may provide control and feedback by exchanging data between footswitch 204 and instrument host 202, between software subsystems within the instrument host, between the instrument host and subsystems external to instrument host 202 and/or GUI host 201, or between subsystems external to instrument host 202 and/or GUI host 201. Instrument host 202 may include various programs and functionality, including but not limited to applications functioning to conduct an ophthalmic surgical procedure.

A surgeon can provide for different parameters or functions to be effectuated by footswitch 204 using GUI host 201. For example, one surgeon may wish to establish phaco power to be provided along the pitch axis and fluid flow in the yaw axis, and she may prefer to employ his right foot and increase fluid flow by turning his foot inward only, such that movement to the right provides no functionality or represents a dead band or dead zone. She may wish, for example, for zero to 40 percent deflection to represent a linear ultrasonic power curve or response having a first slope, from 40 percent to 80 percent a second linear ultrasonic power curve having a second slope, and anything over 80 percent deflection representing full available power. The surgeon or another user may make these indications via GUI host 101 and the footswitch operates as programmed.

The issue arises when footswitch 101 develops nonlinearities or unwanted dead bands, where further motion is not read by the device. As noted, such nonlinearities and dead zones are undesirable.

The present design employs a semi-automated calibration technique to account for issues with various footswitches. The present design may not address all issues with footswitch calibration, as any footswitch may completely fail in a particular aspect, i.e. the yaw axis may be completely nonresponsive due to a mechanical failure. However, many less dramatic failures or nonlinearities may be addressed by the present design. The present design is not limited to a dual axis footpedal, but may be employed on a single axis footpedal or any single axis device, and thus may be employed with a device having at least one axis of control or movement.

Figure 3:
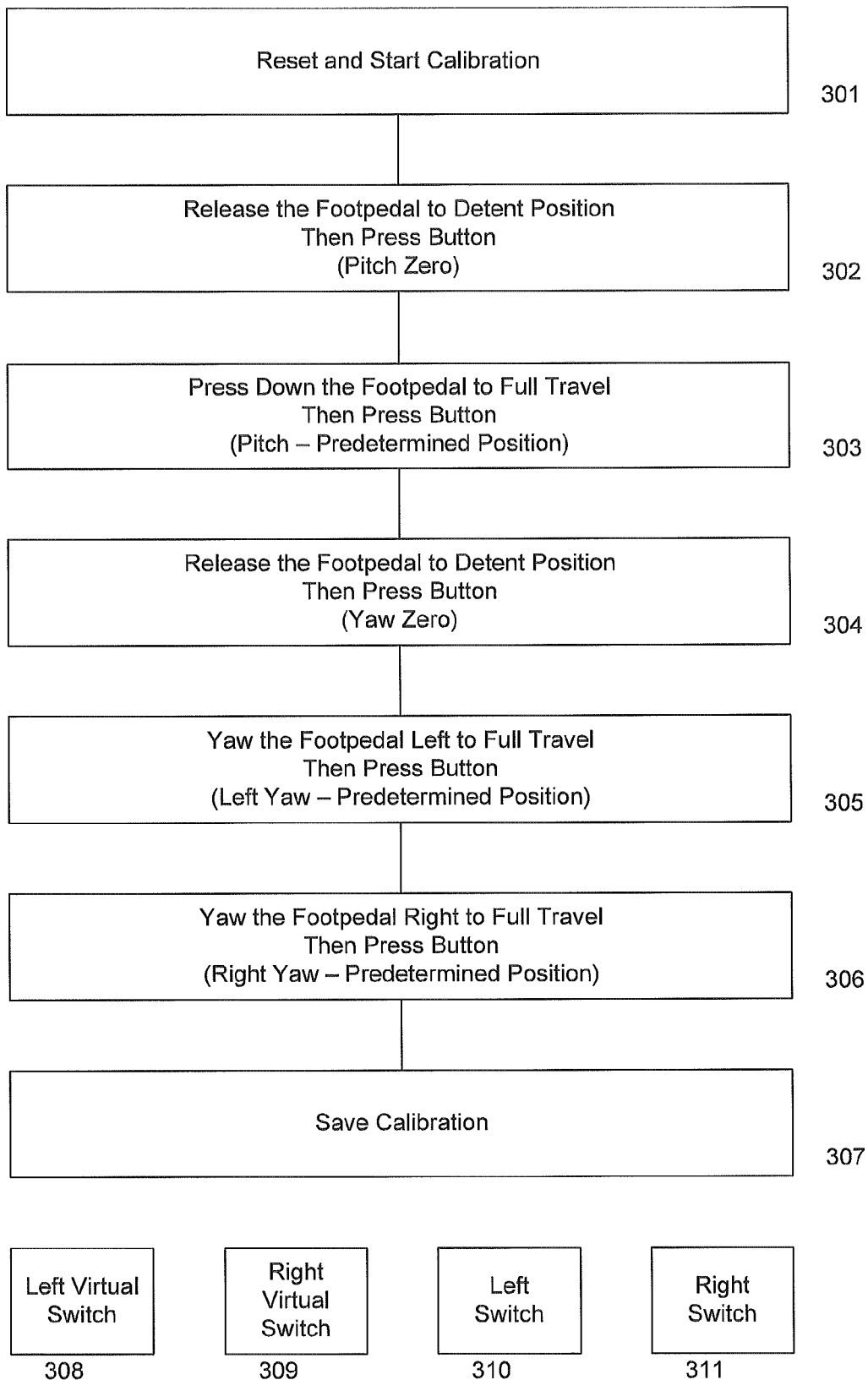
FIG. 3 shows operation of the present design.

FIG. 3 illustrates a general flowchart of the present design for a dual axis footpedal. The same general functions described may be used for a single axis footpedal for the direction of movement available, e.g. calibrating only the pitch or yaw movement of a single axis footpedal. From FIG. 3, seven general functions may be performed by the user at instrument host 201 using graphical user interface host 202 to calibrate the footpedal and minimize the consequences of nonlinearities and dead zones. Point 301 presents the option to the user of resetting and starting calibration. Resetting causes the footpedal and associated hardware, firmware, and/or software to be altered to a factory setting or known parameter set. One of the typical results of resetting is establishing the neutral or center point, the point at which the footpedal returns when not engaged by a foot or other device. By selecting point 301, the user is verifying that the footpedal (not shown in this view) is properly connected to instrument host 202 and the user wishes to reset any settings and begin the calibration process.

Point 302 asks that the footpedal be released to the detent position, such as released all the way to the zero degree pitch position. This position is sometimes referred to as the neutral position. A software button is provided through the GUI host 201, such as by a touchscreen indication or selectable button using GUI host 201. Once the footpedal has been released or provided to the known detent position, or neutral position, again here the zero degree pitch position, the user pushes the button. This establishes the zero degree pitch position or detent position. The detent position may be any known position of the footpedal, including a 10 percent movement, a 50 percent movement or a 100 percent (fully depressed) position, or otherwise. The desire is to establish a known position and begin with that known position, typically in the pitch axis but possibly in the yaw axis if desired.

Point 303 asks the user to press all the way down on the footpedal to full travel position and then press a button shown on the GUI screen or otherwise presented. Again, while full pitch position may be the desired position for point 303, some other position may be employed, where point 302 is the 100 percent position and point 303 is the zero percent position, or the user could be asked to move from the 100 percent position at point 302 to the 50 percent position or some other intermediate position at point 303. In any configuration, a beginning point and a target point is provided and the user is prompted to move from the initial point at point 302 to the target point at point 303

Also, a graphical depiction of the footpedal reading may be provided, such as a zero percent to 100 percent bar graph with target footpedal position indicated, e.g. by a line at 100 percent. In this manner, the user can observe the reading being made, and if a failure exists at the detent position, for example, she may be presented with a failure indication. For example, if no reading is available at 100 percent pitch position, once the user presses the footpedal to the 100 percent position and no signal is received, an indication of no signal received from the pedal may be provided to the user.

While not shown in FIG. 3, the position attained during execution of point 303 instructions may be displayed, such as via GUI host 101, such as in percentage terms in numbers from 0 to 100. Thus, if going from 0 through 100, the GUI may display "50" when the pedal travels through the halfway point, for example. At the completion of point 303, the user may press the button or indicator. The system, via instrument host 202, maintains the reading generated as well as the response received while traveling from the zero position to the 100 position in the arrangement shown.

Point 304 requests a release to the detent or neutral position, which is the case of a dual axis footpedal is the same position as in point 302. Again, the user is asked to push a button or make an indication when the footpedal has been returned to the detent position.

While these tasks are ongoing, the system monitors the footpedal travel and identifies any irregularities, such as the aforementioned nonlinearities or dead zones. If the pedal is at the zero position and the user is instructed to depress the pedal to the 100 percent depressed position, the system may read the angle of depression while going from the zero position to the 100 percent position and may note any angles where the signal drops or is otherwise irregular. These readings may also be maintained in the instrument host.

The completion of point 304 and pressing of the button by the user indicates that the user's foot has been removed and the pedal is back at the neutral position in the embodiment shown. This can be used to indicate the zero yaw position or the starting yaw position. Point 305 instructs the user to yaw the footpedal left to a full travel position and press the button or indicator. Again, instrument host 202 may record or note the intermediate positions going from zero yaw to full left yaw, and while not shown in FIG. 3, the amount of left yaw may be displayed to the user, i.e. graphically indicated, such as by providing on GUI host 201 a number between zero and 100, with zero representing the neutral position and 100 representing full left yaw movement.

Point 306 indicates that the user is to yaw the footpedal to a full right position and press the button or indicator. Again, right and left may be reversed in points 305 and 306 with the same results, and footpedal travel positions or angles may be recorded and/or maintained by the instrument host. While not shown in FIG. 3, the amount of right yaw may be displayed, i.e. graphically indicated, such as by providing a number on GUI host 201, with zero representing the neutral yaw position and 100 representing full right yaw movement. Once the user presses the button or indicator after completing point 306, all relevant positions of the footpedal have been evaluated and the system may process the information received as discussed below.

At point 307, the user may save the calibration, and this typically occurs after the foregoing footpedal position actions are processed by the application operating inside instrument host 202. Date and time of the calibration may be saved on a device, such as an EEPROM in the footpedal or on instrument host 202. The raw calibration data may be saved, or alternately modified calibration data may be saved if the calibration application discussed herein is run after point 306. Further, the response curve or curves provided, whether raw or modified, may be applied to the device and provide the raw or modified response when the device is employed. In other words, the calibration data, raw or modified, may be provided to the instrument host and the instrument host may effectuate response functionality according to the raw or modified response curves when footpedal 204 is employed.

Note that if some point in the calibration process, points 301 through 306, is judged to be inadequate, that point may be repeated if desired by the application. Thus if insufficient information is obtained in one axis, i.e. the user pressed the button before the yaw pedal had reached 100 percent left deflection, the application may direct the user to repeat the desired action, either immediately after the action or once all actions have been completed.

As shown in FIG. 3, other information about other switches may be gathered and considered by the application. Left virtual switch 308, right virtual switch 309, left switch 310, and right switch 311 may be polled during the calibration process, or separate from the calibration process, to see if these switches operate properly. Virtual switches are when the foot pedal is programmed to act a switch. For example, the left yaw movement and/or the right yaw movement of the footpedal may act as a switch as opposed to linear control. Since these are simple switches and are either on or off, simple depression of the switch may provide all of the information needed and may be verified by the user such as via the GUI host 201. The success or failure of the switch, i.e. switch response, may be displayed to the user, and she may be provided the option of flagging a failed switch if desired. If a switch has failed, there is typically nothing that can be done to account for this failure other than to swap out the failed electronic or mechanical components. No compensation may be provided due to a switch or virtual switch failure.

Calibration Application

Once all the data has been collected, the calibration application, typically residing in instrument host 202, may process the data received from the calibration process performed by the user. The calibration application may either be a software module separate from software or hardware monitoring footpedal position, or the calibration application may monitor the footpedal position and save or maintain the responses encountered. Thus the calibration application may have been operating throughout the procedures of FIG. 3, recording and/or maintaining the positions of the device when the various points have been executed by the user.

In operation, the monitoring function, either as apart of the calibration or as a separate module, determines footpedal positions in both pitch and yaw axes in the case of a dual linear footpedal. The footpedal may include hardware, firmware, and/or software that provides A/D (analog to digital) counts of footpedal positions, such as from a low of zero for undeflected to 255 for full deflection in each axis. In the case of firmware performing this function in the footpedal, the firmware may provide footpedal counts to the calibration application operating within instrument host 202. The calibration application may convert the counts into percentages if desired.

Figure 4A:
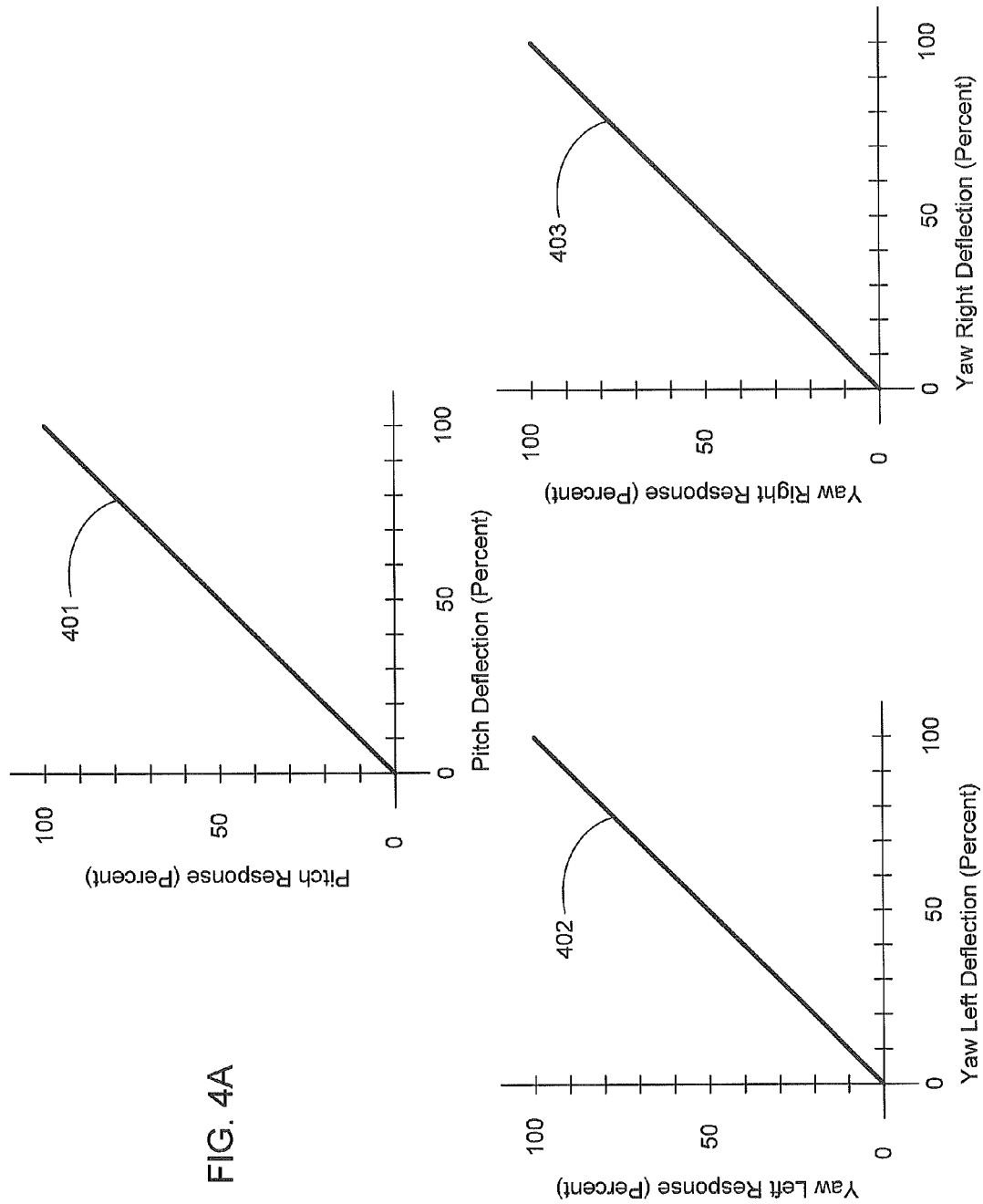
FIG. 4A illustrates perfect or ideal responses of the device in the pitch and yaw axes.

Performance plots that may be encountered during the calibration procedure of FIG. 3 are illustrated in FIGS. 4A-4D. FIG. 4A illustrates perfect or ideal performance of the pitch and yaw axes, shown as response curves 401, 402, and 403 for pitch, yaw left, and yaw right, respectively. For a deflection of zero in the pitch axis, a response of zero is encountered. For a full deflection or 255 counts of actual deflection in the footpedal, a response of 100 percent is encountered. Yaw right and left response representations in FIG. 4A illustrate similar perfect performance.

Figure 4B:
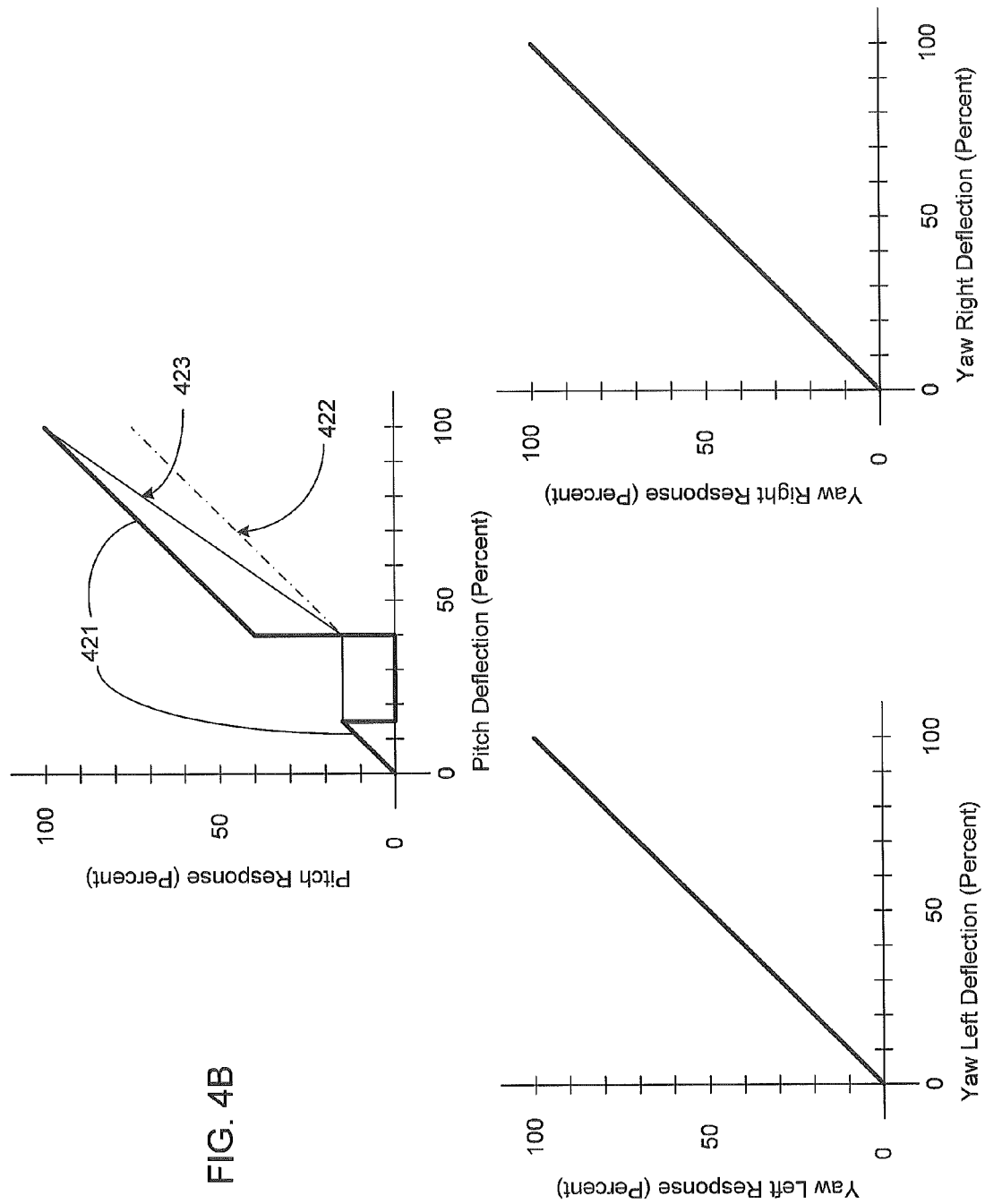
FIG. 4B represents a response including a dead band or dead zone and compensation for the dead band or dead zone.

FIG. 4B shows imperfect performance in the form of response curve 421, where the signal drops between about 40 and 100 counts of deflection in the footpedal, indicating a failure in this region, electrical and/or mechanical. Such a zone is exaggerated for illustrative purposes only; an actual zone of failure covering approximately 25 percent of the entire region would in many cases be considered a complete failure of the device. In this circumstance, the application may define between 40 and 100 counts as a dead band, where deflection in this region is of no consequence, or provides no response, and if the response is graphically presented to the user during the FIG. 3 calibration, a zero or default response may be provided. In operation, without calibration, no response would be received and no functionality provided by the instrument host 202.

The user or the calibration application can make accommodations for the dead band if desired. For example, the user may wish to provide the raw response knowing that the dead band exists, which may be conveyed graphically via the GUI. In such a circumstance, response 421 would be the response curve employed with the device.

Alternately, the user may wish to provide a substantially uniform response in view of the dead band, continuing the response signal from the point where the signal enters the dead band as shown by curve 422. This allows the user to simply skip the dead area and continue to increase performance after encountering the dead band. The resultant curve may be a simple response translation such as curve 422 or may be a recomputation of the response to, for example, provide full response at full deflection (100 percent response at 100 percent pitch deflection) as shown by curve 423.

Thus in the case of dead bands, the system and the calibration application may seek to ignore the problem region or may compensate for the problem area using the application.

Figure 4C:
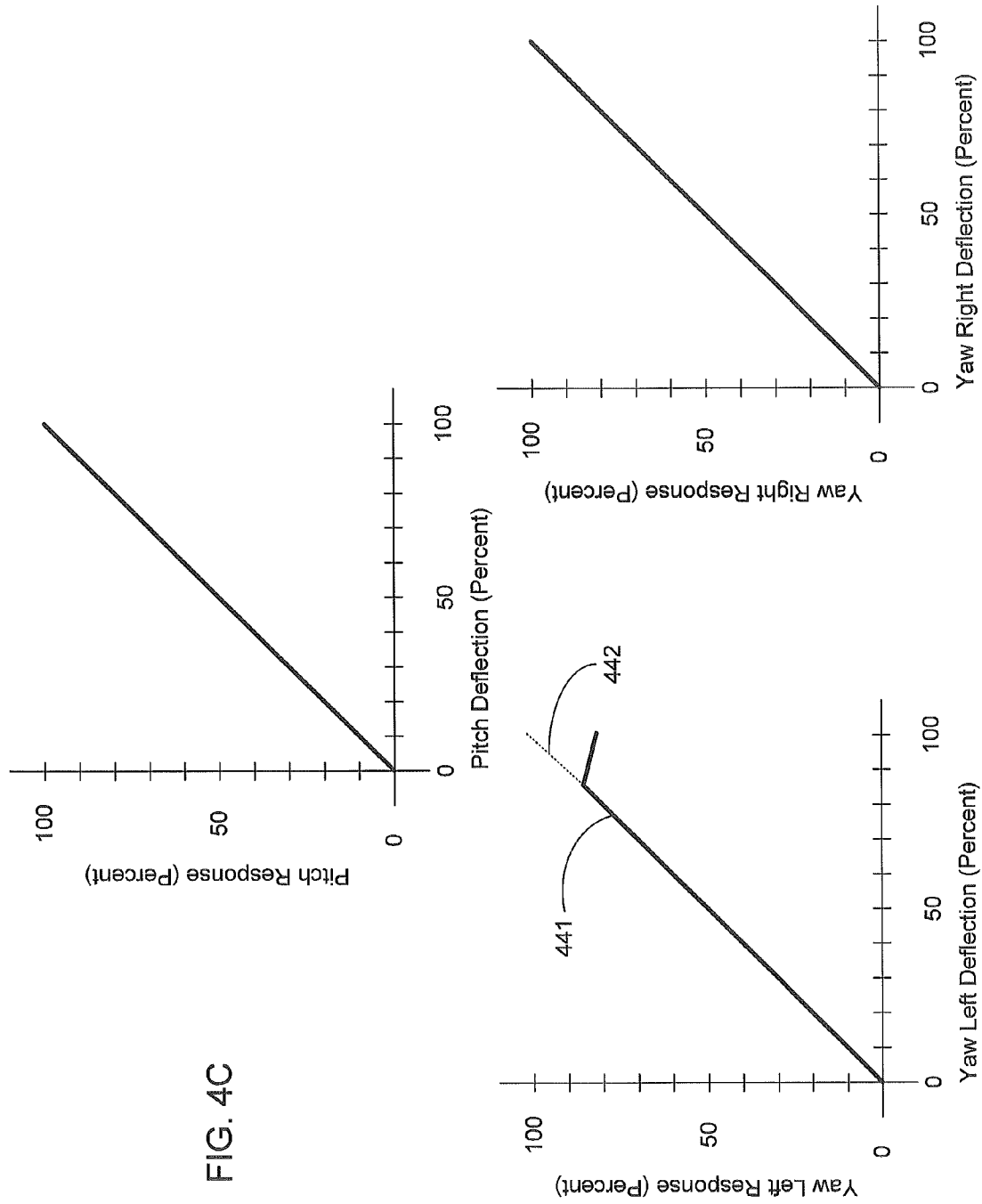
FIG. 4C shows a response including a nonlinear region and compensation for the nonlinearity.

An alternate issue is shown in FIG. 4C, namely the issue of nonlinearity. Curve 441 shows a nonlinearity from approximately 220 counts of left yaw to approximately 255 counts of left yaw. The application may address this nonlinearity by correcting for the nonlinearity in the affected region, as shown by curve 442. The compensation may be applied via the instrument host such that when, in the case of FIG. 4C, the footpedal is deflected to 90 percent, 90 percent response is generated rather than 82 percent were the uncompensated left yaw curve employed.

Figure 4D:
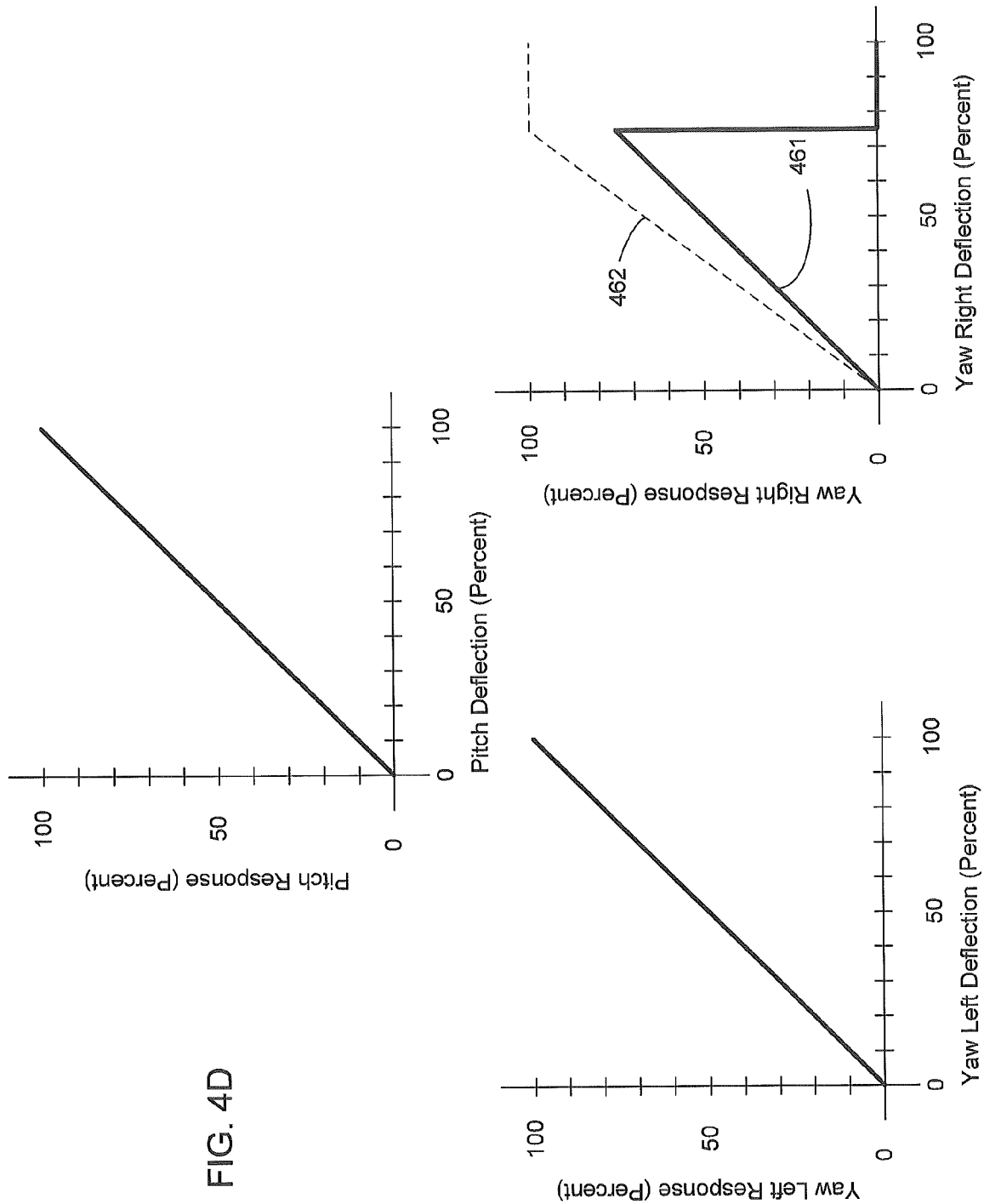
FIG. 4D illustrates a device unable to attain a maximum value and compensation for the inability to achieve the maximum value.

A related issue is shown in FIG. 4D, wherein the full position of right yaw is unachievable as represented by curve 461 (again exaggerated for illustrative purposes). This may result from a dead band at the maximum position when evaluated at point 306 in FIG. 3 and may have been identified during the calibration process performed by the user. The calibration application may address an inability to achieve full position by either ignoring the full position or considering the highest readable/achievable position, in FIG. 4D being approximately the 75 percent point or 192 counts of right yaw, as the maximum position. The application then redefines the performance curve as curve 462, providing a full range from zero to 100 percent from zero counts to 192 counts.

While single issues or irregularities are shown in FIGS. 4B-4D, multiple irregularities may be encountered in multiple axes, and multiple issues may be encountered in a single axis. The representations in these Figures are not accurate depictions of what would be encountered but are for illustrative purposes only, and more, fewer, or different issues may be present in the response curves produced during the calibration process disclosed herein.

The final performance or response curves may be generated by the calibration application, by the user, or by a combination of both. The user may be presented with selections from the calibration application via the GUI and may select these, or the calibration application may account for the irregularities with no user intervention via a set of established criteria for dealing with the issues encountered. Alternately, if a certain number of issues are encountered, such as a specified percentage of a particular curve being unattainable or uncalibrated, or unable to be calibrated, the footpedal may be considered unusable.

Assuming footpedal irregularities may be addressed via the foregoing application and/or user interaction, point 307 in FIG. 3 may enable the user to either save the raw curves generated or the modified curves generated and thus save the calibration. Saving may be to a storage device, such as an EEPROM in the footpedal or to the instrument host 202 or other appropriate storage device. The calibration, in the form of raw or modified performance curves, may be employed by the instrument host 202 together with the footpedal to effectuate a desired response when the footpedal is employed and may address irregularities that would otherwise be encountered. As a simple example, if the modified curve indicates that when 75 percent pitch axis deflection is encountered from the footpedal, the response should be 80 percent functionality. The instrument host may indicate, electrically or mechanically, that 80 percent functionality is required. This can be by implemented using a lookup table or a set of factors or by any reasonable means of effectuating the calibration results and achieving the desired functionality when employing the device, e.g. the footpedal.

The result is a calibrated footpedal that can be reused together with the stored calibration parameters. If the user or another individual wishes to recalibrate the device, she may begin from point 301 and progress through the calibration routine, including accommodating for irregularities encountered during the calibration process.

It is to be understood that while the present design has been described with respect to a footpedal, and primarily a dual axis linear footpedal, any type of mission critical device or devices may employ the calibration process described herein. For example, any device having at least one axis of control or movement may be calibrated, again defining minimums and maximums for each axis and asking the user to move the device to the minimum and maximum points. A single axis of movement may be provided in the device and calibrated according to the present design. The system can record movements of the device and based on the inputs provided and the responses encountered may offer the user the ability to address any deficiencies encountered and/or may automatically provide a resultant input and response representation for use with the device. Further, a device having more or fewer axes of control may employ the current design.

The foregoing is not determinative or exclusive or inclusive of all components, interfaces, communications, and operational modes employable within the present design. The design presented herein and the specific aspects illustrated are meant not to be limiting, but may include alternate components while still incorporating the teachings and benefits of the invention, namely a method and device for calibrating a device operative in one or more axes, such as a footpedal or footswitch. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method of calibrating a device operable in at least one axis of movement, comprising:
   providing a host device and a device operable in at least one axis of movement, wherein the device is coupled with the host device;
   instructing a user, via the host device, to operate the device to a first predetermined position in a first axis of movement while concurrently monitoring movement of the device to establish a set of movement responses;
   prompting the user, via the host device, to indicate when the first predetermined position in the first axis is attained;
   modifying the set of movement responses, via the host device, when movement response irregularities are detected, thereby establishing a modified set of movement responses; and
   employing the modified set of movement responses with the device, via the host device.

2. The method of claim 1, wherein said modifying comprises enabling an entity to provide desired response characteristics in establishing the modified set of movement responses.

3. The method of claim 1, wherein said modifying comprises automated processing based on predetermined rules.

4. The method of claim 1, wherein the user indicates when the first predetermined position has been attained by pressing a button.

5. The method of claim 1, further comprising saving the calibration, via the host device, wherein saving the calibration comprises saving the modified set of movement responses on a storage device.

6. The method of claim 1, further comprising evaluating switch performance for at least one switch associated with the device, via the host device.

7. The method of claim 1, wherein the device comprises a footpedal having two axes of movement.

8. The method of claim 1, wherein the host device comprises a graphical user interface.

9. An apparatus comprising:
   a medical device operable in at least one axis of movement; and
   a host device coupled with the medical device comprising:
   a monitor configured to monitor movement of the medical device in the at least one axis of movement and establish a set of movement responses of the medical device; and
   an application configured to receive the set of movement responses from the monitor and modify the set of movement responses when movement response irregularities are detected, thereby establishing a modified set of movement responses;
   wherein the modified set of movement responses is configured to be employed with the medical device.

10. The apparatus of claim 9, wherein the application interacts with a user through a user interface coupled with the instrument host to enable said user to provide desired response characteristics in establishing the modified set of movement responses.

11. The apparatus of claim 9, wherein the application computes the modified set of user responses based on predetermined rules.

12. The apparatus of claim 9, wherein the host device further comprises a graphical user interface configured to instruct a user to operate the medical device to at least one predetermined device position in the at least one axis of movement.

13. The apparatus of claim 12, wherein the host device provides a desired position and the graphical user interface enables the user to indicate when the desired position is attained.

14. The apparatus of claim 13, wherein the graphical user interface provides a button for the user to engage when the desired position has been attained.

15. The apparatus of claim 9, wherein the medical device comprises an electronic storage unit configured to save calibrations, wherein saving the calibration comprises saving the modified set of movement responses.

16. The apparatus of claim 9, wherein the medical device comprises a footswitch having two axes of movement.

17. A method of calibrating a medical device operable in at least one axis of movement, comprising:
   providing a host device and a medical device operable in at least one axis of movement, wherein the medical device is coupled with the host device;
   instructing a user, via the host device, to operate the medical device beginning at a first point along at least one axis of movement;
   prompting the user, via the host device, to indicate when the first point along the at least one axis of movement has been reached;
   instructing the user, via the host device, to operate the medical device to a second point along the at least one axis of movement;
   prompting the user, via the host device, to indicate when the second point along the at least one axis of movement has been reached;
   monitoring movement of the medical device during said instructing and prompting, via the host device, wherein said monitoring produces a set of movement responses;
   selectively modifying the set of movement responses based on encountered movement response irregularities to a modified set of movement responses, via the host device; and
   employing the modified set of movement responses when employing the medical device during a medical procedure, via the host device.

18. The method of claim 17, wherein said selectively modifying comprises enabling an entity to provide desired response characteristics in establishing the modified set of movement responses.

19. The method of claim 17, wherein said selectively modifying comprises automated processing of the set of movement responses based on predetermined rules.

20. The method of claim 17, wherein the user indicates when the desired position has been attained by pressing a button.

21. The method of claim 17, further comprising saving the calibration, via the host device, wherein saving the calibration comprises saving the modified set of movement responses on a storage device.

22. The method of claim 17, further comprising evaluating switch performance for at least one switch associated with the device, via the host device.

23. The method of claim 17, wherein the device comprises a footpedal having two axes of movement.

24. A method for calibrating a device operable in at least one axis of movement, comprising:
   providing a host device and a device operable in at least one axis of movement, wherein the device is coupled with the host device;
   placing the device in a first predetermined position within a first axis;
   confirming the first predetermined position upon reaching the position, via the host device;
   placing the device in a second pre-determined position within the first axis,
   confirming the second predetermined position upon reaching the position, via the host device;
   monitoring movement from the first predetermined position to the second predetermined position to establish a set of movement responses, via the host device;
   detecting irregularities in the movement from the first predetermined position to the second predetermined position, via the host device;
   modifying the set of movement responses, via the host device, based on the detected irregularities; and
   employing the modified set of movement responses with the device, via the host device.

25. The method of claim 24, further comprising:
   placing the device in a first predetermined position within a second axis;
   confirming the first predetermined position within the second axis upon reaching the position, via the host device;
   placing the device in a second predetermined position within the second axis;
   confirming the second predetermined position within the second axis upon reaching the position, via the host device;
   monitoring movement from the first predetermined position to the second predetermined position within the second axis to establish a second set of movement responses, via the host device;
   detecting irregularities in the movement from the first predetermined position to the second predetermined position within the second axis, via the host device;
   modifying the second set of movement responses, via the host device, based on the detected irregularities; and
   employing the modified second set of movement responses with the device, via the host device.

* * * * *